United States Patent
Wong et al.

(10) Patent No.: US 10,107,748 B2
(45) Date of Patent: Oct. 23, 2018

(54) OPTICAL SENSING DEVICE FOR SURFACE PLASMON RESONANCE (SPR) AND OPTICAL SENSING METHOD USING SURFACE PLASMON RESONANCE (SPR)

(71) Applicant: Agency for Science, Technology and Research, Singapore (SG)

(72) Inventors: Chi Lok Wong, Singapore (SG); Malini Olivo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 15/033,981

(22) PCT Filed: Nov. 4, 2014

(86) PCT No.: PCT/SG2014/000517
§ 371 (c)(1),
(2) Date: May 3, 2016

(87) PCT Pub. No.: WO2015/065292
PCT Pub. Date: May 7, 2015

(65) Prior Publication Data
US 2016/0313246 A1 Oct. 27, 2016

(30) Foreign Application Priority Data
Nov. 4, 2013 (SG) .................. 201308173

(51) Int. Cl.
*G01N 21/55* (2014.01)
*G01N 21/552* (2014.01)
*G01N 21/21* (2006.01)

(52) U.S. Cl.
CPC ........... *G01N 21/553* (2013.01); *G01N 21/21* (2013.01); *G01N 2201/0683* (2013.01); *G01N 2201/12* (2013.01)

(58) Field of Classification Search
CPC ......... G01N 21/553; G01N 2201/0683; G01N 2201/12; G01N 21/65; G01N 2021/655; G01N 21/47; G01N 2201/063; G01N 2201/0691
USPC ................. 356/445–446, 301, 300, 517, 481
See application file for complete search history.

(56) References Cited

U.S. PATENT DOCUMENTS

| 5,485,277 A | 1/1996 | Foster |
| 7,233,396 B1* | 6/2007 | Hall ...................... G01N 21/21 356/369 |

(Continued)

OTHER PUBLICATIONS

Wong et al., "Multiplex Spectral Surface Plasmon Resonance Imaging (SPRI) Sensor Based on the Polarization Control Scheme," Optics Express, vol. 19, No. 20, Sep. 26, 2011, pp. 18965-18978.

(Continued)

*Primary Examiner* — Isiaka Akanbi
(74) *Attorney, Agent, or Firm* — Winstead, P.C.

(57) ABSTRACT

An optical sensing device is provided, including a first polarizer, a second polarizer, wherein the first polarizer and the second polarizer have respective transmission axes aligned in orthogonal directions, an SPR sensor arrangement including an SPR sensing surface, the SPR sensor arrangement arranged to receive an incident light beam passed through a polarizer to be reflected at the SPR sensing surface and transmitted through a second polarizer to provide a transmitted light beam, a detector arrangement configured to detect the transmitted light beam, the transmitted light beam including a sensing signal and a reference signal, and a processor electrically coupled to the detector arrangement, the processor configured to perform a subtraction operation between the sensing signal and the reference signal. The optical sensing is based on a differential measurement scheme. The subtraction between the sensing signal and the reference signal cancels the common path noise and enhances the sensor resolution.

18 Claims, 10 Drawing Sheets

(56) References Cited

U.S. PATENT DOCUMENTS

| | | | |
|---|---|---|---|
| 2006/0211024 A1 | 9/2006 | Corn et al. | |
| 2007/0008546 A1 | 1/2007 | Ho et al. | |
| 2007/0166763 A1* | 7/2007 | Ho | G01N 21/553 435/7.1 |
| 2008/0158549 A1 | 7/2008 | Lee et al. | |
| 2011/0292394 A1* | 12/2011 | Wu | G01N 21/553 356/451 |
| 2011/0310383 A1* | 12/2011 | Masson | G02B 5/04 356/319 |
| 2013/0224886 A1 | 8/2013 | Iwasaki et al. | |

OTHER PUBLICATIONS

Wang et al., "A High-Throughput Surface Plasmon Resonance Biosensor Based on Differential Interferometric Imaging," Measurement Science and Technology, vol. 23, 2012, pp. 1-10.

Wong et al., "Colorimetric Surface Plasmon Resonance Imaging (SPRI) Biosensor Array Based on Polarization Orientation," Biosensors and Bioelectronics, vol. 47, 2013, pp. 545-552.

Piliarik et al., "A New Surface Plasmon Resonance Sensor for High-Throughput Screening Applications," Biosensors and Bioelectronics, vol. 20, 2005, pp. 2104-2110.

International Preliminary Report on Patentability for International Application No. PCT/SG2014/000517 dated Aug. 19, 2015, pp. 1-5.

Extended European Search Report for European Patent Application No. 14 858 305.7 dated Jun. 8, 2017, pp. 1-11.

Hooper et al., "Dual-Channel Differential Surface Plasmon Ellipsometry for Bio-Chemical Sensing," Biosensors and Bioelectronics, vol. 25, 2009, pp. 411-417.

Luo et al., "Surface Plasmon Resonance Enhanced Polar Magneto-Optical Kerr Effects for Applications in Current Sensing," Power and Energy Engineering Conference, Asia-Pacific, Mar. 25, 2011, pp. 1-4.

* cited by examiner

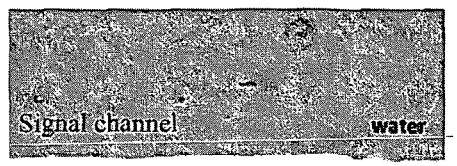
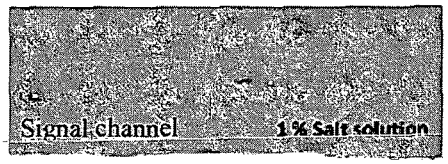
FIG. 6A    FIG. 6B
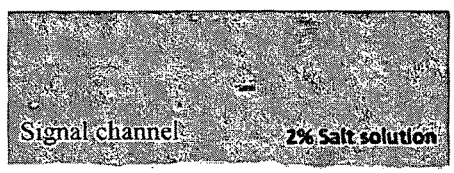
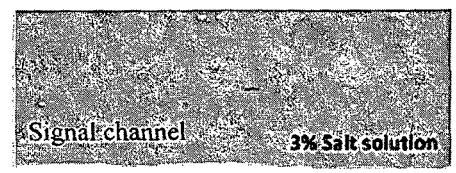
FIG. 6C    FIG. 6D
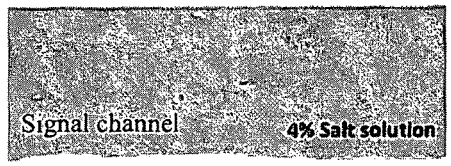
FIG. 6E    FIG. 6F

OPTICAL SENSING DEVICE FOR SURFACE PLASMON RESONANCE (SPR) AND OPTICAL SENSING METHOD USING SURFACE PLASMON RESONANCE (SPR)

CROSS-REFERENCE TO RELATED APPLICATION

This application claims the benefit of priority of Singapore patent application No. 201308173-2, filed 4 Nov. 2013, the content of it being hereby incorporated by reference in its entirety for all purposes.

TECHNICAL FIELD

Various embodiments relate to an optical sensing device for surface plasmon resonance (SPR) and an optical sensing method using surface plasmon resonance (SPR).

BACKGROUND

Protein biomarkers have gained rapid increasing research interests in recent years. Detection of the expression level of protein biomarkers in patient samples enables early disease diagnosis and treatment response assessment. Protein biomarkers for cancers, heart diseases and infectious diseases have been reported to date.

Mass spectroscopy, 2D (two-dimensional) western blotting, 2D (two-dimensional) gel electrophoresis and enzyme-linked immunosorbent assay (ELISA) are the most widely used detection methods for biomarker discovery. Nevertheless, these existing techniques are not compatible with high throughput multiplex analysis. Furthermore, they are all labeling methods, where the use of fluorescent labels or secondary antibodies can interfere with the original biomolecular interactions.

Recently, micro-array technology has become an effective alternative for high throughput profiling. The applications of antibody microarray for high throughput proteomics studies and antibody have been demonstrated, and is by far the most widely used probe for biomarker profiling. Direct target labeling, sandwich assay and competitive adsorption assay are common strategies for antibody microarray detection, in which fluorescent labeling, secondary antibodies or enzyme are required in the detection process. In antibody array detection, different fluorescently labeled molecules or secondary antibodies are required for each array element. Large scale multiplexed measurements are therefore limited by the availability of corresponding fluorescent labels or secondary antibodies.

Surface plasmon resonance (SPR) is a non-labeling detection alternative. It measures the refractive index changes associated with bio-molecular bindings occurring at the gold sensing surface. Conventional SPR imaging sensors measure the intensity distribution of the reflection beam with a CCD (charge-coupled device) detector. The major limitation of conventional intensity SPR imaging sensors is the limited sensor resolution ($10^{-5}$ RIU). In recent years, spectral based SPR imaging sensor with the scanning of surface plasmon excitation minimum is reported, however the sensor resolution is limited ($10^{-5}$ RIU) and time-consuming scanning is required during measurement. In the inventors' previous research, the inventors imaged the color texture variations caused by the SPR absorption minimum shift and the system was applied to image the refractive index changes of lubricant at highly pressurized contact. Nevertheless, the sensor resolution is also limited.

SUMMARY

According to an embodiment, a optical sensing device for surface plasmon resonance (SPR) is provided. The optical sensing device may include a first polariser, a second polariser, wherein the first polariser and the second polariser have respective transmission axes aligned in orthogonal directions, an SPR sensor arrangement including an SPR sensing surface, the SPR sensor arrangement arranged to receive an incident light beam passed through the first polariser to be reflected at the SPR sensing surface and transmitted through the second polariser to provide a transmitted light beam, a detector arrangement configured to detect the transmitted light beam, the transmitted light beam including a sensing signal and a reference signal, and a processor electrically coupled to the detector arrangement, the processor configured to perform a subtraction operation between the sensing signal and the reference signal.

According to an embodiment, an optical sensing method using surface plasmon resonance (SPR) is provided. The method may include providing a sample to an SPR sensing surface of an SPR sensor arrangement, passing a light through a first polariser to provide an incident light beam to be received by the SPR sensor arrangement, reflecting the incident light beam at the SPR sensing surface to provide a reflected light beam, transmitting the reflected light beam through a second polariser to provide a transmitted light beam, wherein the first polariser and the second polariser have respective transmission axes aligned in orthogonal directions, detecting the transmitted light beam, the transmitted light beam including a sensing signal and a reference signal, and performing a subtraction operation between the sensing signal and the reference signal.

According to an embodiment, an optical sensing device for surface plasmon resonance (SPR) is provided. The optical sensing device may include a first polariser, a second polariser, wherein the first polariser and the second polariser have respective transmission axes aligned in orthogonal directions, an SPR sensor arrangement including an SPR sensing surface, the SPR sensor arrangement arranged to receive an incident light beam passed through the first polariser to be reflected at the SPR sensing surface and transmitted through the second polariser to provide a transmitted light beam, and an optics arrangement configured to split the transmitted light beam into a p-polarisation beam and an s-polarisation beam, and a detector arrangement configured to detect the p-polarisation beam and the s-polarisation beam.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 4A shows an example of a colorimetric SPR image obtained, while

FIG. 5C shows a plot of a sensing signal and a correlated reference signal, based on the results shown in FIG. 5B, while

FIGS. 6A to 6F show colorimetric SPR images for different salt solution samples.

DETAILED DESCRIPTION

Figure 1A:
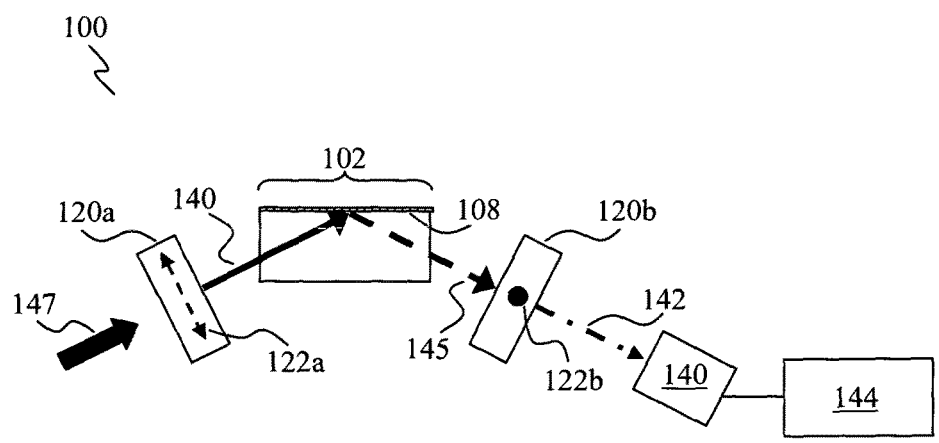
FIG. 1A shows a schematic cross-sectional view of an optical sensing device for surface plasmon resonance (SPR), according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may provide surface plasmon resonance (SPR) sensors with differential response schemes. Each SPR sensor may employ a differential response scheme.

Various embodiments may provide a portable colorimetric surface plasmon resonance (SPR) imaging sensor based on polarisation orientation and a differential measurement scheme.

Various embodiments may provide a differential measurement based colorimetric surface plasmon resonance (SPR) imaging sensor. The differential measurement scheme improves the measurement stability, which may enhance the imaging sensor resolution by approximately 1 order of magnitude.

Various embodiments may provide one or more of the following:

(1) A differential measurement based colorimetric SPR imaging sensor based on or employing polarisation orientation (for example, see FIGS. 1A, 1B, 2A to 2D, and 3 to be described later).

(2) The application of Hue colour space for the quantification of colour changes in spectral SPR images (for example, see FIGS. 4A and 4B to be described later). This may allow pixel to pixel conversion, which may provide real time 2D (two-dimensional) resolution spectral SPR imaging for high throughput microarray detection.

(3) A differential measurement scheme for spectral SPR imaging, e.g., a differential measurement scheme involving a signal channel and a reference channel, or a differential measurement scheme between p- and s-polarisations. The differential measurement may be carried out in the time domain.

(4) A portable all-in-one SPR imaging sensor device, e.g., having a real-time display, image storage means (e.g., SD (Secure Digital) card/microSD card/other flash memory devices), external signal or data transmission means (e.g., wifi/other mobile signal connections and USB connection) and an image processing unit (for example, see FIG. 2C to be described later).

(5) A bio-sensing/sensing chip (e.g., antibody array, DNA (deoxyribonucleic acid) array and RNA (ribonucleic acid) array) integrated with a portable SPR imaging sensor device for diseases diagnosis, food safety, biomarkers detection, cancer detection, gas/volatile organic compounds detection, blood testing and environmental monitoring applications (for example, see FIG. 2D to be described later).

(6) Application of a portable SPR imaging sensor device for point of care (POC) detection.

The sensor or sensing device of various embodiments may be used in many different areas, including but not limited to drug discovery, analytical detection applications, environmental detections, etc.

In order to enhance the sensor resolution, various embodiments may provide two designs of surface plasmon resonance (SPR) sensors based on two different differential response schemes. For example, various embodiments may provide an SPR imaging sensor based on a differential response between the signal and reference sensing areas (for example, see FIG. 2A to be described later), and an SPR imaging sensor based on a differential response between p- and s-polarisation beams (for example, see FIG. 3 to be described later).

A colorimetric surface plasmon resonance (SPR) imaging sensor based on or employing polarisation orientation will now be described by way of the following non-limiting examples.

The imaging sensor or optical sensing device of various embodiments may measure the spectral characteristic variation caused by the steep phase change occurring at surface plasmon excitation. A surface plasmon resonance (SPR) prism coupler may be placed in between two polarisers with perpendicular transmission axes, where the transmission of the incident beam (e.g., including light from an excitation light source) is forbidden or blocked. At the excitation wavelength of surface plasmon, a phase difference may be introduced between the p- and s-polarisation components of the light. The phase difference may rotate the orientation angle of the polarisation ellipse of the light, and the light interacting with the surface plasmon may be allowed to pass through the crossed polarisers setting. As the momentum of the surface plasmon wave only matches with a particular wavelength range, a particular spectral profile may be produced, which may be associated with the steep phase response at surface plasmon excitation. This method may enhance the sensitivity of a conventional spectral based SPR sensor through probing the steep phase response at surface plasmon resonance.

Consider an elliptically polarised light $\vec{E}$ and the two orthogonal optical disturbances (p- and s-components), which may be represented as, $$E_s = E_{so} \cos(kz - \omega t) \quad \text{(Equation 1),}$$

$$E_p = E_{po} \cos(kz - \omega t + \varphi) \quad \text{(Equation 2),}$$

where $E_s$ refers to the electric field of s-polarization, $E_{so}$ refers to maximum electric field of s-polarization, k refers to the Boltzmann constant, z refers to wave displacement, $\omega$ refers to angular frequency, t refers to time, $E_p$ refers to the electric field of p-polarization, $E_{po}$ refers to maximum electric field of p-polarization, and $\varphi$ is the relative phase difference between the two orthogonal optical disturbances (p- and s-wave).

The elliptically polarised light $\vec{E}$ may be further described by the following equation of ellipse:

$$\left(\frac{E_p}{E_{po}}\right)^2 + \left(\frac{E_s}{E_{so}}\right)^2 - 2\left(\frac{E_p}{E_{po}}\right)\left(\frac{E_s}{E_{so}}\right)\cos\varphi = \sin^2\varphi. \quad \text{(Equation 3)}$$

The elliptically polarised light $\vec{E}$ also makes an orientation angle $\alpha$ with the ($E_s$, $E_p$) coordinate system such that $$\tan 2\alpha = \left(\frac{2 E_{so} E_{po}}{E_{so}^2 - E_{po}^2}\right) \cos\varphi. \quad \text{(Equation 4)}$$

A phase difference, $\Delta\phi$, between the p- and s-polarisations is produced at surface plasmon excitation, as provided below $$\Delta\phi = (\phi_p - \phi_s) \quad \text{(Equation 5).}$$

where $\phi_p$ refers to the phase shift in p-polarization (or response of p-polarization), and $\phi_s$ refers to the phase shift in s-polarization (or response of s-polarization).

Therefore, the wave vector of $\vec{E}$ may be modified as $$E_s = E_{so} \cos(kz - \omega t) \quad \text{(Equation 6),}$$

$$E_p{}' = E_{po} \cos(kz - \omega t + \varphi + \Delta\phi) \quad \text{(Equation 7),}$$

Based on equations 6 and 7, the equation of the elliptically polarised light $\vec{E}$ and the angle with the ($E_s$, $E_p$) coordinate system may also be modified, as shown below $$\left(\frac{E_p'}{E_{po}}\right)^2 + \left(\frac{E_s}{E_{so}}\right)^2 - 2\left(\frac{E_p'}{E_{po}}\right)\left(\frac{E_s}{E_{so}}\right)\cos(\varphi + \Delta\phi) = \sin^2(\varphi + \Delta\phi), \quad \text{(Equation 8)}$$

$$\tan 2\alpha' = \left(\frac{2 E_{so} E_{po}}{E_{so}^2 - E_{po}^2}\right) \cos(\varphi + \Delta\phi). \quad \text{(Equation 9)}$$

Various embodiments may enable spectral SPR imaging relying on the colour change caused by spectral response variation, which may correspond to the differential phase change, $\Delta\phi$, between p-polarisation (or p-polarisation wave or beam) and s-polarisation (or s-polarisation wave or beam), as described above.

Various embodiments of the optical sensing devices will now be described by way of the following non-limiting examples.

FIG. 1A shows a schematic cross-sectional view of an optical sensing device 100 for surface plasmon resonance (SPR), according to various embodiments. The optical sensing device 100 includes a first polariser 120a, a second polariser 120b, wherein the first polariser 120a and the second polariser 120b have respective transmission axes 122a, 122b aligned in orthogonal directions, an SPR sensor arrangement 102 including an SPR sensing surface 108, the SPR sensor arrangement 102 arranged to receive an incident light beam 140 passed through the first polariser 120a to be reflected at the SPR sensing surface 108 and transmitted through the second polariser 120b to provide a transmitted light beam 142, a detector arrangement 140 configured to detect the transmitted light beam 142, the transmitted light beam 142 including a sensing signal and a reference signal, and a processor 144 electrically coupled to the detector arrangement 140, the processor 144 configured to perform a subtraction operation between the sensing signal and the reference signal.

In other words, an optical sensing device 100 (e.g., a differential measurement based optical sensing device) may be provided. The optical sensing device 100 may be employed for SPR imaging or sensing. The optical sensing device 100 may include a first polariser 120a having a transmission axis, as represented by the dashed double-headed arrow 122a, aligned in a first direction. The first polariser 120a may receive a light 147, which may be polarised by the first polariser 120a to provide an incident light beam 140 at the output side of the first polariser 120a. This may mean that the incident light beam 140 is a light beam that has been polarised by the first polariser 120a, meaning a light beam that has been transmitted through the first polariser 120a. The incident light beam 140 may have polarisation at least substantially aligned with the transmission axis 122a.

The optical sensing device 100 may include a second polariser 120b having a transmission axis, as represented by the circular dot 122b, aligned in a second direction, e.g., into and/or out of the paper. The transmission axes 122a, 122b may be aligned at least substantially perpendicular to each other, or at least substantially 90° relative to each other. This may mean that the transmission axis 122a aligned in a first direction and the transmission axis 122b aligned in a second direction may be at least substantially orthogonal to each other. In this way, the first polariser 120a and the second polariser 120b may form a pair of cross polarisers.

The optical sensing device 100 may further include an SPR sensor arrangement 102 having an SPR sensing surface 108. The SPR sensor arrangement 102 may be arranged such as to receive the incident light beam 140, where the incident light beam 140 may be reflected by or at the SPR sensing surface 108 to provide a reflected light beam 145. For example, the incident light beam 140 may be reflected by or at the SPR sensing surface 108 via total internal reflection (TIR). The reflected light beam 145 may be transmitted through the second polariser 120b to provide a transmitted light beam 142. This may mean that the SPR sensor arrangement 102 may be arranged in between the first polariser 120a and the second polariser 120b, for example, in an optical path between the first polariser 120a and the second polariser 120b. The reflected light beam 145 may be polarised by the second polariser 120b to provide the transmitted light beam 142 at the output side of the second polariser 120b. This may mean that the transmitted light beam 142 is a light beam that has been polarised by the second polariser 120b, meaning a light beam that has been transmitted through the second polariser 120b. The transmitted light beam 142 may have polarisation at least substantially aligned with the transmission axis 122b.

The optical sensing device 100 may further include a detector arrangement 140 configured to receive the transmitted light beam 142. The transmitted light beam 142 may include a sensing signal and a reference signal. In this way, the detector arrangement 140 may detect the sensing signal and the reference signal. In various embodiments, the detector arrangement 140 may include a colour CCD (charge-coupled device) detector or a CCD camera.

The optical sensing device 100 may further include a processor 144 electrically coupled to the detector arrangement 140. The processor 144 may receive the sensing signal and the reference signal and may perform a subtraction operation between the sensing signal and the reference signal to generate a differential signal. For example, the processor 144 may subtract the reference signal from the sensing signal to generate a differential signal (e.g., differential signal=sensing signal−reference signal).

In the context of various embodiments, the phrase "transmission axis" may refer to a "polarising axis". A light beam passing through a polariser may be converted into a polarised light beam having polarisation aligned along the transmission axis of the polariser.

In the context of various embodiments, the phrase "SPR sensor arrangement" as used herein may include or may refer to an arrangement configured for surface plasmon resonance and generation of surface plasmon waves (which are electromagnetic waves).

In the context of various embodiments, the phrase "SPR sensing surface" as used herein may include or may refer to a surface where surface plasmon resonance may occur such that a surface plasmon wave may be generated on or along the surface, in response to illumination of the surface with an excitation signal (e.g., an optical signal or light) or incident photons, for example, the incident light beam 140, at a resonant condition, due to, for example, the material of the SPR sensing surface. The surface plasmon wave may propagate along the SPR sensing surface.

In the context of various embodiments, the phrase "sensing signal" as used herein may include or may refer to a signal that may carry information, for example, related to an SPR-related event, e.g., corresponding to a molecular or bio-molecular interaction. The sensing signal may also carry noise information related to the optical sensing device.

In the context of various embodiments, the phrase "reference signal" as used herein may include or may refer to a signal that may carry noise information related to the optical sensing device. A reference signal may refer to a control signal.

In the context of various embodiments, at least one of the sensing signal or the reference signal may be in the form of an SPR image.

In the context of various embodiments, the differential signal resulting from the subtraction between the sensing signal and the reference signal may be free of the noise information.

In various embodiments, the SPR sensor arrangement 102 may include a prism, and wherein the SPR sensing surface 108 may be provided on a base (or an outer base surface) of the prism. The SPR sensing surface 108 may interface with the base (or outer base surface) of the prism. The SPR sensing surface 108 may be coated or deposited on the base (or outer base surface) of the prism.

In various embodiments, the SPR sensor arrangement 102 may include an SPR-active element, and wherein a surface of the SPR-active element may define the SPR sensing surface 108. The SPR-active element may be provided on a base (or an outer base surface) of the prism of the SPR sensor arrangement 102. A surface of the SPR-active element interfacing with the base (or outer base surface) of the prism may define the SPR sensing surface 108. In the context of various embodiments, the phrase "SPR-active element" as used herein may include or may refer to an element that is configured for surface plasmon resonance and generation of surface plasmon waves, where a surface plasmon wave may be generated at a surface thereof, in response to illumination of the surface of the SPR-active element with an excitation signal, e.g. the incident light beam 140, at a resonant condition, for example due to the material of the surface or the material of the SPR-active element. An SPR-active element may include at least one metal.

In various embodiments, the SPR-active element may include a film structure, e.g., a metal film structure. The film structure may include a gold (Au) layer (e.g., a single gold layer). The film structure may include a gold (Au) layer and a silver (Ag) layer arranged one over the other, with the gold layer being arranged proximal to the base of the prism.

In various embodiments, the SPR sensor arrangement 102 may further include a sampling substrate in fluid communication with the SPR sensing surface 108. The sampling substrate may be employed to flow in one or more samples. In various embodiments, the sampling substrate may be or may include a flow cell (e.g. a micro-fluidic flow cell).

In various embodiments, a sensing area (e.g., a signal channel, or a signal area) and a reference area (e.g., a reference channel, or a control area) may be defined on the SPR sensing surface 108, and wherein the sensing signal may originate from the sensing area and the reference signal may originate from the reference area. In various embodiments, the sensing area may be employed for sensing an SPR-related event, for example, the sensing area may include a sensitive material such as an antibody that may bind complementarily to a corresponding antigen to be sensed as an SPR-related event. In various embodiments, the reference area may be maintained at least substantially pristine, as a control. For example, this may mean that the reference area may be at least substantially free of a sensitive material such as an antibody.

In various embodiments, the optical sensing device 100 may further include a polarising beam splitter (e.g., a Wollaston prism) configured to split the transmitted light beam 142 into a p-polarisation beam to define the sensing signal, and an s-polarisation beam to define the reference signal. In the context of various embodiments, the phrase "p-polarisation beam" may mean a beam having polarisation that occurs parallel to the plane of incidence, while the phrase "s-polarisation beam" may mean a beam having polarisation that occurs perpendicular to the plane of incidence.

In various embodiments, the detector arrangement 140 may include a first detector configured to detect the p-polarisation beam, and a second detector configured to detect the s-polarisation beam. In various embodiments, at least one of the first detector or the second detector may be or may include a photodiode. In various embodiments, at least one of the first detector or the second detector may be or may include a CCD (charge-coupled device) detector or a CCD camera, e.g., a colour CCD detector or camera.

In various embodiments, the optical sensing device 100 may further include a first focusing lens (e.g., an objective lens) arranged to focus the p-polarisation beam onto the first detector, and a second focusing lens (e.g., an objective lens) arranged to focus the s-polarisation beam onto the second detector.

In various embodiments, the optical sensing device 100 may further include a quarter-wave ($\lambda/4$) plate arranged in an optical path between the SPR sensor arrangement 102 and the second polariser 120*b*.

In various embodiments, the optical sensing device 100 may further include a light source configured to provide a light (e.g., 147) for generating the incident light beam 140.

In various embodiments, the light source may include or may be a broad band light source, for example, a broad band white light source, e.g., a halogen lamp, or one or more white light emitting diodes (LEDs). The broad band light source may be configured to emit light having a wavelength range of between about 400 nm and about 800 nm, for example, a wavelength range of between about 400 nm and about 600 nm, or a wavelength range of between about 600 nm and about 800 nm.

In various embodiments, the light source may include or may be a laser source. The laser source may be an infrared (IR) laser source. The laser source may be configured to emit light having a wavelength of about 850 nm or more (e.g., ≥850 nm), for example, ≥900 nm, or ≥950 nm.

In various embodiments, the optical sensing device 100 may further include focusing optics (e.g., a focusing lens, or an objective lens) arranged to focus the transmitted light beam 142 to the detector arrangement 140.

In various embodiments, the optical sensing device 100 may further include collimation optics configured to generate a collimated light (e.g., 147) to be received by the first polariser 120*a*. The collimation optics may receive a light and collimates the light. The collimation optics may also act as a beam expander, e.g., the collimation optics may receive a light and collimates and expands the light. In various embodiments, the collimation optics may include an objective lens and a bi-concave lens. The bi-concave lens may act as a beam expander.

In various embodiments, the processor 144 may be further configured to extract respective Hue component values from the sensing signal and the reference signal based on a Hue-Saturation-Value colour space model prior to performing the subtraction operation. In this way, the subtraction operation may be performed based on the respective Hue component values from the sensing signal and the reference signal.

In various embodiments, the optical sensing device 100 may further include an analogue-to-digital circuit (or analogue-to-digital converter, ADC) electrically coupled in between the detector arrangement 140 and the processor 144.

In the context of various embodiments, the optical sensing device 100 may be a portable optical sensing device.

In the context of various embodiments, the optical sensing device 100 may further include a display for displaying at least one of the sensing signal or the reference signal. In various embodiments, the differential signal may be displayed. The display may be a liquid crystal display, e.g., an LCD/TFT (thin-film-transistor)/IPS (in-plane switching) display.

In the context of various embodiments, the optical sensing device 100 may further include signal (or data) transmission means (e.g., wifi transmission means).

In the context of various embodiments, the optical sensing device 100 may further include a storage device or a memory device. The storage device or the memory device may be removable from the optical sensing device 100.

In the context of various embodiments, the optical sensing device 100 may further include a USB (Universal Serial Bus) interface.

In the context of various embodiments, the optical sensing device 100 may further include a power source (e.g., a battery).

In the context of various embodiments, the optical sensing device 100 may be a colorimetric surface plasmon resonance (SPR) imaging sensor based on polarisation orientation and a differential measurement scheme.

Figure 1C:
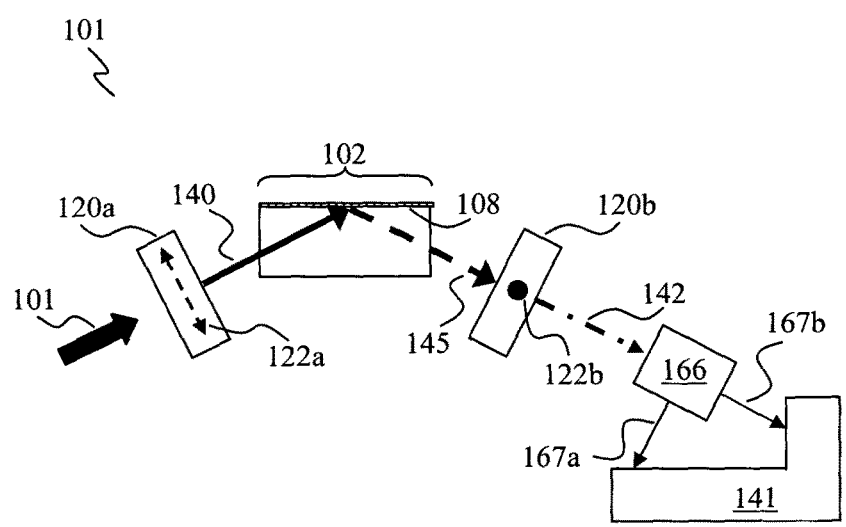
FIG. 1C shows a schematic cross-sectional view of an optical sensing device for surface plasmon resonance (SPR), according to various embodiments.
Figure 1B:
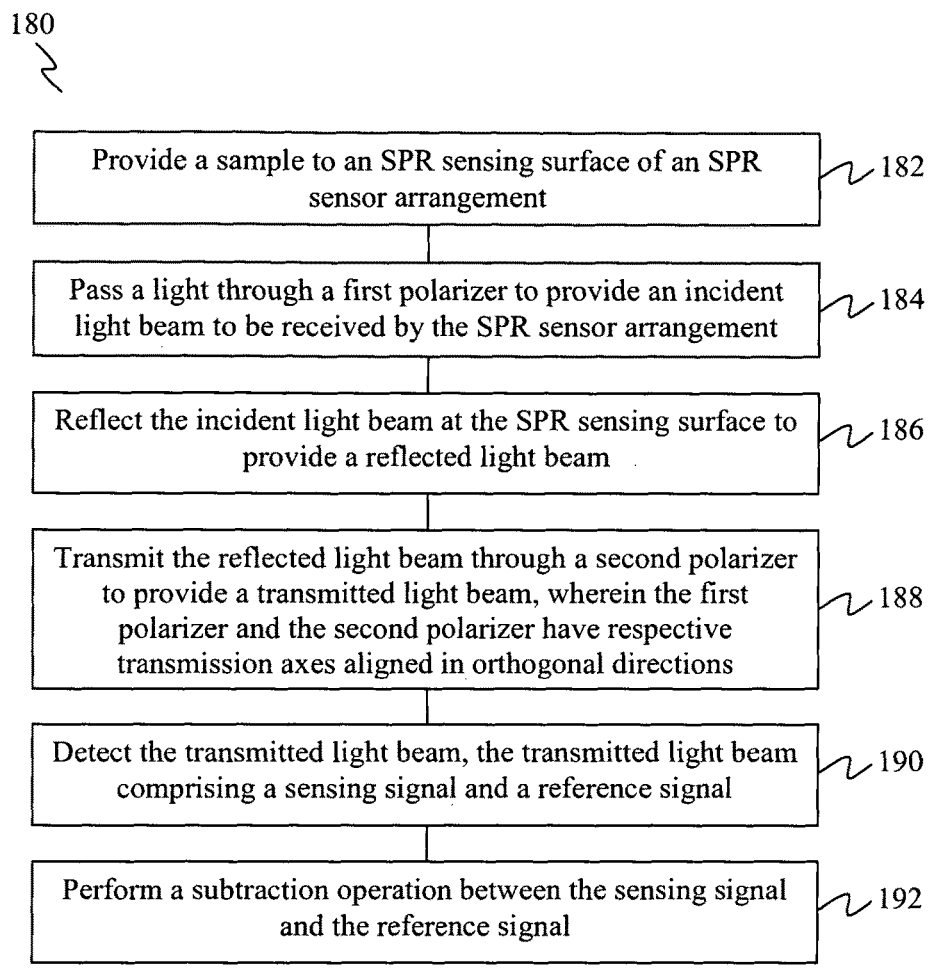
FIG. 1B shows a flow chart illustrating an optical sensing method using surface plasmon resonance (SPR), according to various embodiments.

FIG. 1B shows a flow chart 180 illustrating an optical sensing method using surface plasmon resonance (SPR), according to various embodiments.

At 182, a sample is provided to an SPR sensing surface of an SPR sensor arrangement.

At 184, a light is passed through a first polariser to provide an incident light beam to be received by the SPR sensor arrangement.

At 186, the incident light beam is reflected at the SPR sensing surface to provide a reflected light beam. For example, the incident light beam may be reflected at or by the SPR sensing surface via total internal reflection (TIR).

At 188, the reflected light beam is transmitted through a second polariser to provide a transmitted light beam, wherein the first polariser and the second polariser have respective transmission axes aligned in orthogonal directions.

At 190, the transmitted light beam is detected, the transmitted light beam including a sensing signal and a reference signal.

At 192, a subtraction operation is performed between the sensing signal and the reference signal. For example, the reference signal may be subtracted from the sensing signal In this way, a differential signal may be obtained or generated.

Accordingly, in various embodiments, a differential measurement based optical sensing method using surface plasmon resonance (SPR) may be provided In various embodiments, the method may further include focusing the transmitted light beam, for example, to a detector arrangement, or onto a detector.

In various embodiments, the SPR sensor arrangement may include a prism, and wherein the SPR sensing surface may be provided on a base of the prism.

In various embodiments, a sensing area (e.g., a signal channel) and a reference area (e.g., a reference channel) may be defined on the SPR sensing surface, and wherein the sensing signal may originate from the sensing area and the reference signal may originate from the reference area. This may mean that the incident light beam may be reflected at the sensing area (e.g., signal channel) and the reference area (e.g., a reference channel) of the SPR sensing surface to provide the reflected light beam.

In various embodiments, the method may further include splitting the transmitted light beam into a p-polarisation beam to define the sensing signal, and an s-polarisation beam to define the reference signal. In various embodiments, at 190, detecting the transmitted light beam may include detecting the p-polarisation beam (e.g., using a first detector) and the s-polarisation beam (e.g., using a second detector).

In various embodiments, the method may further include focusing the p-polarisation beam, for example, onto a first detector, and focusing the s-polarisation beam, for example, onto a second detector.

In various embodiments, the method may further include passing the reflected beam through a quarter-wave ($\lambda/4$) plate.

In various embodiments, the method may further include collimating the light to be passed through the first polariser.

In various embodiments, the method may further include expanding the light to be passed through the first polariser.

In various embodiments, the light to be provided to the first polariser may have a wavelength range of between about 400 nm and about 800 nm, for example, a wavelength range of between about 400 nm and about 600 nm, or a wavelength range of between about 600 nm and about 800 nm.

In various embodiments, the light to be provided to the first polariser may include a laser light. This may mean that the light beams as described (e.g., incident light beam, reflected light beam, etc.) may be laser beams.

In various embodiments, the laser light may have a wavelength of about 850 nm or more (e.g., ≥850 nm), for example, ≥900 nm, or ≥950 nm. This may mean that the laser light may be infrared (IR) laser light.

In various embodiments, the method may further include extracting respective Hue component values from the sensing signal and the reference signal based on a Hue-Saturation-Value colour space model prior to performing the subtraction operation at 192. In this way, the subtraction operation may be performed based on the respective Hue component values from the sensing signal and the reference signal.

In various embodiments, the method may further include displaying at least one of the sensing signal, or the reference signal. Further, the differential signal may be displayed.

While the method described above is illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

FIG. 1C shows a schematic cross-sectional view of an optical sensing device 101 for surface plasmon resonance (SPR), according to various embodiments. The optical sensing device 101 includes a first polariser 120a, a second polariser 120b, wherein the first polariser 120a and the second polariser 120b have respective transmission axes aligned in orthogonal directions, an SPR sensor arrangement 102 including an SPR sensing surface 108, the SPR sensor arrangement 102 arranged to receive an incident light beam 140 passed through the first polariser 120a to be reflected at the SPR sensing surface 108 and transmitted through the second polariser 120b to provide a transmitted light beam 142, and an optics arrangement 166 configured to split the transmitted light beam 142 into a p-polarisation beam 167a (e.g., to define a sensing signal), and an s-polarisation beam 167b (e.g., to define a reference signal), and a detector arrangement 141 configured to detect the p-polarisation beam 167a and the s-polarisation beam 167b.

In various embodiments, the optical sensing device 101 may be a differential measurement based optical sensing device for surface plasmon resonance (SPR).

In various embodiments, the optics arrangement 166 may include a polarising beam splitter (e.g., a Wollaston prism).

In various embodiments, the detector arrangement 141 may include a first detector configured to detect the p-polarisation beam 167a, and a second detector configured to detect the s-polarisation beam 167b.

In various embodiments, the SPR sensor arrangement 102 may include a prism, and wherein the SPR sensing surface 108 may be provided on a base of the prism.

In various embodiments, the optical sensing device 101 may further include a laser source configured to provide a light for generating the incident light beam 140. The laser source may be an infrared (IR) laser source. The laser source may be configured to emit light having a wavelength of about 850 nm or more (e.g., ≥850 nm), for example, ≥900 nm, or ≥950 nm.

In various embodiments, the optical sensing device 101 may further include a processor electrically coupled to the detector arrangement 141, wherein the p-polarisation beam 167a defines a sensing signal, and the s-polarisation beam 167b defines a reference signal, and wherein the processor may be configured to perform a subtraction operation between the sensing signal and the reference signal. In this way, a differential signal may be generated, for example by subtracting the reference signal from the sensing signal.

It should be appreciated that features or components of the optical sensing device 101 that are similarly present in the optical sensing device 100 may be as described in the context of the optical sensing device 100. Further, it should be appreciated that one or more features or components of the optical sensing device 100 may be additionally provided for the optical sensing device 101.

Figure 2A:
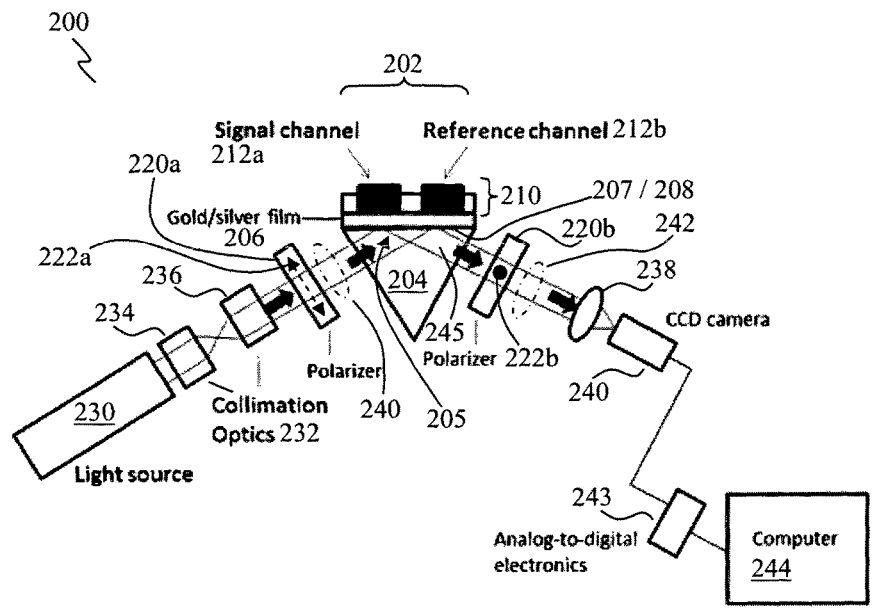
FIG. 2A shows a schematic view of an optical sensing device, according to various embodiments.

FIG. 2A shows a schematic view of an optical sensing device or system 200, according to various embodiments. The sensing device 200 may be a surface plasmon resonance (SPR) imaging sensor, for example, a spectral SPR imaging sensor. The sensing device 200 may employ a method of differential response between signal and reference sensing areas for SPR detection.

The sensing device 200 may include an SPR sensor arrangement 202 for sensing or detecting SPR-related events, for example, molecular or bio-molecular interactions, with the help of surface plasmons. The SPR sensor arrangement 202 may include a prism (e.g., a glass prism) 204, which may act as an SPR prism coupler, and an SPR-active element 206 provided at the base 205 of the prism 204. The SPR-active element 206 may provide an SPR sensing surface 208 which may interface with the prism 204, e.g., interface with the prism base 205. The SPR-active element 206 may include a metal film or metal film structure, for example coated or deposited on the base 205 of the prism 204. As non-limiting examples, the SPR-active element 206 may include a gold layer or a gold/silver film, meaning a gold (Au) layer and a silver (Ag) layer arranged one over the other. The gold layer may be arranged proximate to the prism 204.

The SPR sensor arrangement 202 may further include a sampling substrate 210. The sampling substrate 210 may, for example, be a PDMS (Polydimethylsiloxane)-based microfluidic flow cell attached to or on the SPR sensing surface 208 for feeding in samples with different refractive index values. The sampling substrate 210 may include at least one signal sensing area (or signal channel, or sensing channel) 212a and at least one reference sensing area (or reference channel) 212b. The signal sensing area (or signal channel) 212a may mean an area or position of the sampling substrate 210 where an SPR-related event (e.g., a bio-molecular interaction) may occur such that a corresponding sensing signal related to the SPR-related event may be collected. The reference sensing area (or reference channel) 212b may mean an area or position of the sampling substrate 210 where no SPR-related event is expected, such that a signal related to background noise, for example, may be collected.

The sensing device 200 may include a pair of polarisers: a first polariser (input polariser) 220a and a second polariser (output polariser) 220b. The prism 204 may be placed in between the two polarisers 220a, 220b. The prism 204 may be optically coupled with the two polarisers 220a, 220b such that the prism 204 is positioned in an optical path between the two polarisers 220a, 220b. The first polariser 220a may have a transmission axis, represented by the double-headed arrow 222a, along a first direction such that a light beam exiting or transmitted through the first polariser 220a may be polarised in a direction at least substantially parallel to the transmission axis 220a. The second polariser 220b may have a transmission axis, represented by the circular dot 222b, along a second direction that is at least substantially perpendicular to the transmission axis 222a of the first polariser 220a. This may mean, for example, that the transmission axis 222b of the second polariser 220b may be along a direction into or out of the paper. Therefore, the angle between the transmission axes 222a, 222b of the two polarisers 220a, 220b may be about 90 degrees. It should be appreciated that the transmission axes 222, 222b may be oriented in any directions as long as the transmission axes 222, 222b are aligned at least substantially perpendicular or orthogonal to each other so that the two polarisers 220a, 220b may form cross polarisers. In this way, the angle of rotation of the first polariser 220a and the second polariser 220b may be chosen to be perpendicular to each other.

The sensing device 200 may further include a light source 230 which may provide a light beam (or an excitation signal) towards the SPR sensor arrangement 202. The light source 230 may be a broad band light source, for example, a white light source (e.g., one or more white LEDs) or a halogen illuminator (e.g., a halogen lamp). As a non-limiting example, the light source 230 may provide light in a wavelength range of about 400 nm to about 800 nm, e.g., using a halogen lamp. In various embodiments, due to the application of a range of wavelengths (e.g., 400 nm-800 nm), the spectral profile variation in the whole visible spectrum may be measured or obtained.

The light beam emitted from the light source 230 may be collimated and expanded by lenses. For example, the sensing device 200 may include collimation optics 232 having an objective lens (e.g., a 10× objective lens) 234 and a bi-concave lens 236 to collimate and expand the light beam produced by the light source 230. The light beam may then propagate through the first polariser 220a to provide an incident beam 240 towards the SPR sensor arrangement 202. The collimated incident beam 240 may be incident or impinge on the total internal reflection surface 207 at the base 205 of the prism 204 having the SPR-active element 206 (for example, having a gold sensing layer or a silver/gold sensing layer) with the SPR sensing surface 208. This may mean that, after passing through the first polariser 220a, the polarised incident beam 240 may interact with or enter the SPR-active element 206 (e.g., a gold or silver/gold sensing layer) coated on the prism (e.g., a glass prism) 204. Light that is reflected, e.g. reflected light beam 245, may be transmitted towards the second polariser 220b. As the two polarisers 220a, 220b form cross polarisers, the original or initial incident beam (e.g., broad band incident beam) 240 cannot be transmitted through the second polariser 220b.

At (or close to) the excitation wavelength of a surface plasmon wave, the incident beam 240 impinging on the base surface 207 of the prism 204 may cause generation of a surface plasmon wave at the SPR sensing surface 208 of the SPR-active element 206 that interfaces with the base 205 of the prism 204. At (or close to) the excitation wavelength of the surface plasmon wave, a phase difference $\Delta\phi$ may be introduced between the p-polarisation component and the s-polarisation component of the light. This may mean that, for a light portion of the incident beam that corresponds to the surface plasmon excitation wavelength or excitation spectral range, the p-polarisation component and the s-polarisation component of this light portion may experience a phase difference $\Delta\phi$. As described in equation 9, the orientation angle, $\alpha'$, of the ellipse may be shifted correspondingly and the rotation of the ellipse allows the light portion 242 interacting with the surface plasmon to be transmitted through the second polariser 220b. In this way, the light portion 242 may form a transmitted light beam. At wavelength out of the excitation spectral range, the interaction with the surface plasmon wave is weak and the ellipse is almost parallel to the original orientation angle of the incident beam 240, and therefore no significant transmitting light is observed in the wavelength region longer or shorter than the excitation wavelength.

The light portion (or transmitted light beam) 242 may be focused by a focusing lens (e.g., an objective lens) 238, and thereafter detected or captured by a colour detector (e.g., a colour CCD detector or a colour CCD camera) 240. The detector 240 may be electrically coupled to analog-to-digital electronics or circuit 243 and to a processor (e.g., a computer, or notebook computer) 244. In this way, the signal produced by the detector 240 may be converted into a digital signal by the analog-to-digital electronics 243 and received by the processor 244, for example, to be stored, displayed, processed, manipulated, or analysed. In various embodiments, the processor 244 may be employed to perform subtraction of the sensing signal from the sensing channel 212a and the reference signal from the reference channel 212b.

The transmitted light beam 242 may provide one or more SPR images, where the resultant SPR images may be captured by a colour CCD camera 240 and may be analyzed using an internally developed software.

Figure 2B:
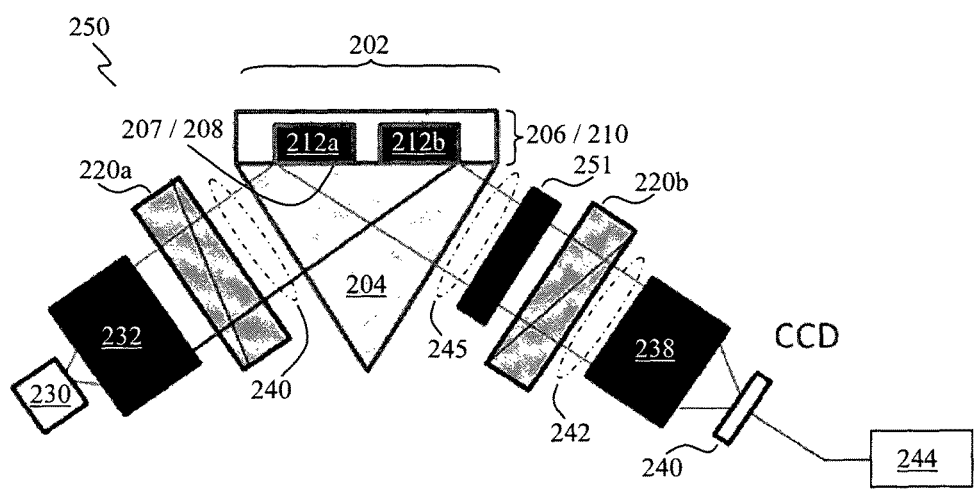
FIG. 2B shows a schematic view of an optical sensing device, according to various embodiments.

While not shown in FIG. 2A, it should be appreciated that a quarter-wave ($\lambda$/4) plate may be arranged between the prism 204 and the second polariser 220b. In this way, the reflected light beam 245 reflected from the prism 204 may pass through the quarter-wave plate and the second polariser 220b. As a non-limiting example, please see FIG. 2B showing a schematic view of an optical sensing device 250 incorporating a quarter-wave (λ/4) plate 251. Like features or components of the sensing device 250 that are similarly present in the sensing device 200 are denoted by like reference numerals and may be as described in the context of the sensing device 200. While not shown in FIG. 2B, the sensing device 250 may also include analog-to-digital electronics as described in the context of the sensing device 200.

A non-limiting example of a differential measurement scheme that may be employed will now be described.

As shown in FIGS. 2A and 2B, a signal channel 212a and a reference channel 212b may be provided on the sensing surface 208. Images from both channels 212a, 212b may be focused onto the same CCD chip and captured simultaneously. Signals from both channels 212a, 212b may experience same/similar instrumentation and environmental noise, and therefore subtraction between the signal and reference images/signals may minimise or eliminate the common noise (or common path noise). As the sensor resolution is equal to (or directly proportional to) the sensor sensitivity times the sensor stability (sensor sensitivity×sensor stability), the minimisation or elimination of noise may eventually produce corresponding enhancement in sensor resolution. Therefore, in this way, the sensor resolution may be enhanced through noise reduction.

Various embodiments of the sensing device (e.g. 200, 250) may incorporate the application of Hue colour space for the quantification of colour changes in spectral SPR images. The Hue component in a HSV/HSI (Hue-Saturation-Value/Hue-Saturation-Intensity) colour space may be applied to quantify the colour information in spectral SPR images, as will be described later below.

The sensing devices 200, 250 may be arranged in a "hand size" casing and may work as an all-in-one portable device for point-of-care (POC) detection and analysis. FIG. 2C shows a schematic view of a portable optical sensing device 254, according to various embodiments, illustrating an all-in-one portable device based on colorimetric SPR imaging, for example, for POC detection. Like features or components of the sensing device 254 that are similarly present in the sensing devices 200, 250 are denoted by like reference numerals and may be as described in the context of the sensing devices 200, 250.

The portable sensing device 254 may further include a micro-processor 255, a LCD display (liquid crystal display) 256 for real-time imaging (an SPR image 257 is shown as an example), a WiFi communication or transmission means 258 and a memory unit or memory device (e.g., a microSD card) 259 for image storage and wireless transfer to a notebook computer or an external processor for further quantified analysis of, for example, binding curves and binding affinity. The portable sensing device 254 may also include a USB (Universal Serial Bus) interface 260.

Figure 2C:
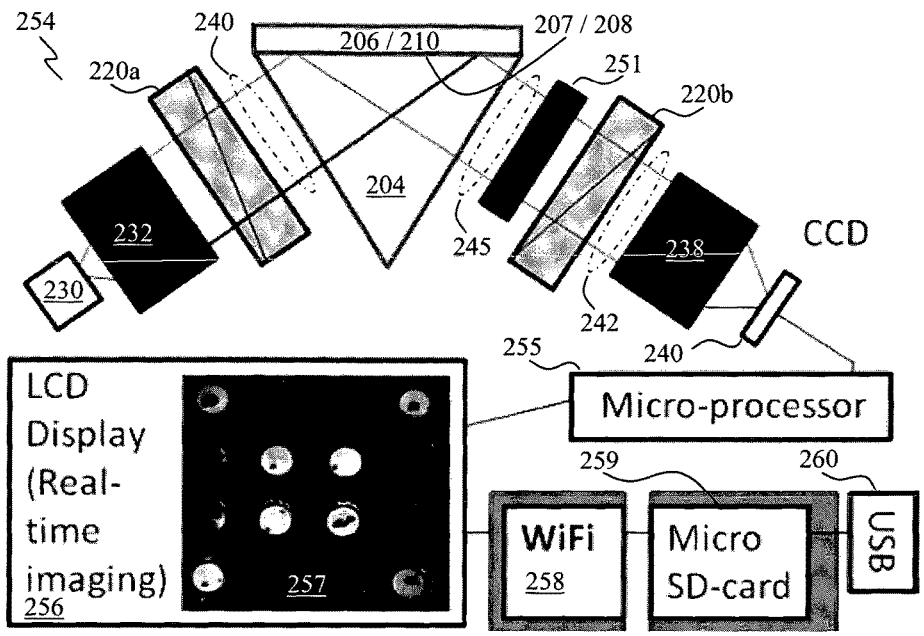
FIG. 2C shows a schematic view of a portable optical sensing device, according to various embodiments.

As shown in FIG. 2C, the all-in-one portable device 254 may integrate the following features or parts: (1) an optical design or optical arrangement for colorimetric SPR imaging; (2) a liquid crystal display 256 (e.g., LCD/TFT (thin-film-transistor)/IPS (in-plane switching)) for real time displaying the SPR imaging information, for example, of the analyte at the sensing surface (e.g., 208); (3) the device 254 may be able to capture, monitor and store all the SPR imaging information during the detection process. The information may be stored in a portable micro-SD/SD/other flash memory (e.g., 259) with (or without) wifi connectivity, for example via wifi communication means 258 and/or the USB interface 260. Integrating the wifi communication means 258 may allow wireless transmission of the SPR imaging videos or images to a notebook or a processor for further calculation on bio-molecular binding curves and binding constants; and (4) the device 254 may be powered by battery for portable POC usages.

While not shown in FIG. 2C, the sampling substrate 210 may include at least one signal channel 212a and at least one reference channel 212b as described in the context of the sensing devices 200, 250. The sensing device 254 may also include analog-to-digital electronics as described in the context of the sensing devices 200, 250.

Figure 2D:
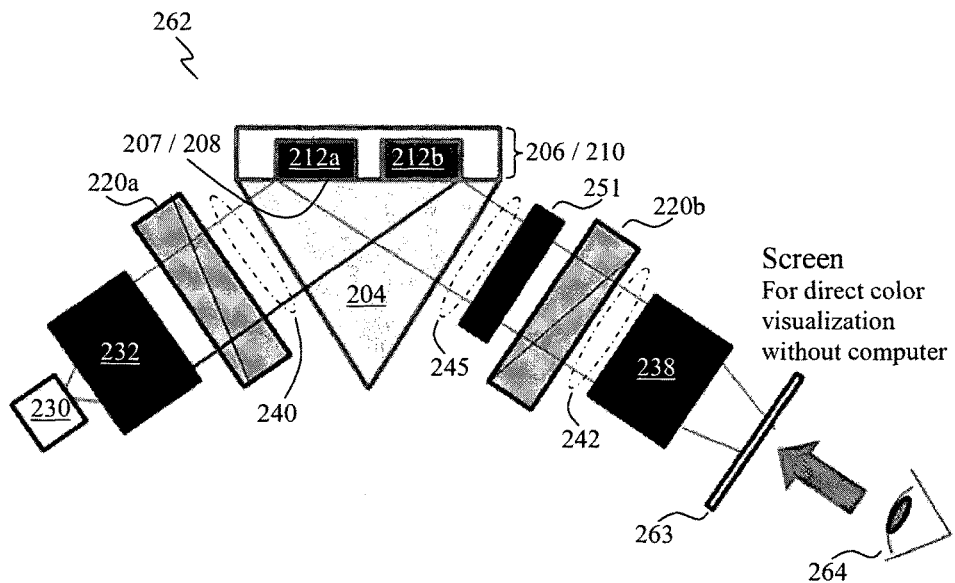
FIG. 2D shows a schematic view of an optical sensing device, according to various embodiments.

FIG. 2D shows a schematic view of an optical sensing device 262, according to various embodiments. The sensing device 262 may provide a low-cost version of the optical design of various embodiments for further cost reduction. Like features or components of the sensing device 263 that are similarly present in the sensing devices 200, 250 are denoted by like reference numerals and may be as described in the context of the sensing devices 200, 250. In the setting of the sensing device 262, the optical SPR image may be directly projected onto a small screen 263 in approximately 1 cm$^2$ for viewing by a user's eye 264. As the SPR information is in the form of optical colour changes, the information may be understood and identified by an untrained person, while conventional intensity, phase, and spectrum scanning based SPR imaging sensors all require a computer, a CCD, a control and analysis software for detection, which collectively may add an additional cost of S$2000 or above to the sensing or imaging system.

In various embodiments, modification of the SPR sensing devices as described above may be carried out, for sensitivity enhancement. For example, the sensitivity of the SPR sensor or sensing device as described in the context of FIGS. 2A to 2D may be enhanced with modifications relating to the light source and/or detector, while the other optical parts of the SPR sensing device may remain the same, as will be described below with reference to FIG. 3.

Briefly, the light source 230 may be replaced by a laser excitation source, which may provide an excitation light with enhanced stability. The detection limit of an SPR device or system is related to the sensor stability as described by the following equation:

$$\text{Detection limit} = \frac{\text{Refractive index change}}{\text{SPR sensor response}} \times \text{Sensor stability}. \quad \text{(Equation 10)}$$

According to Equation 10, a stabilized excitation light source (e.g., a laser) therefore may provide a lower detection limit. Equation 10 may also be expressed as $$\text{resolution} = \frac{\Delta RIU}{\text{response}} (S.D.), \quad \text{(Equation 11)}$$

where (ΔRIU/response) refers to the sensitivity of the sensor. Therefore, a reduced S.D. produces or results in a corresponding sensor resolution improvement.

Further, a photo-diode detector pair with p- and s-polarisation signal subtraction may be provided. The differential scheme as described in the context of the sensing devices 200, 250 (FIGS. 2A and 2B) may be further improved by using a polarising beam splitter to split the p-polarisation signal and the s-polarisation signal. The subtraction between the p-signal and the s-signal cancels the common noise happening at the sensing device and suppresses the system noise so that the sensor detection limit may be enhanced (refer to equation 10). The optical paths of the p-polarisation light and the s-polarisation light may be identical and the common path noise in the sensing device may therefore be eliminated.

Figure 3:
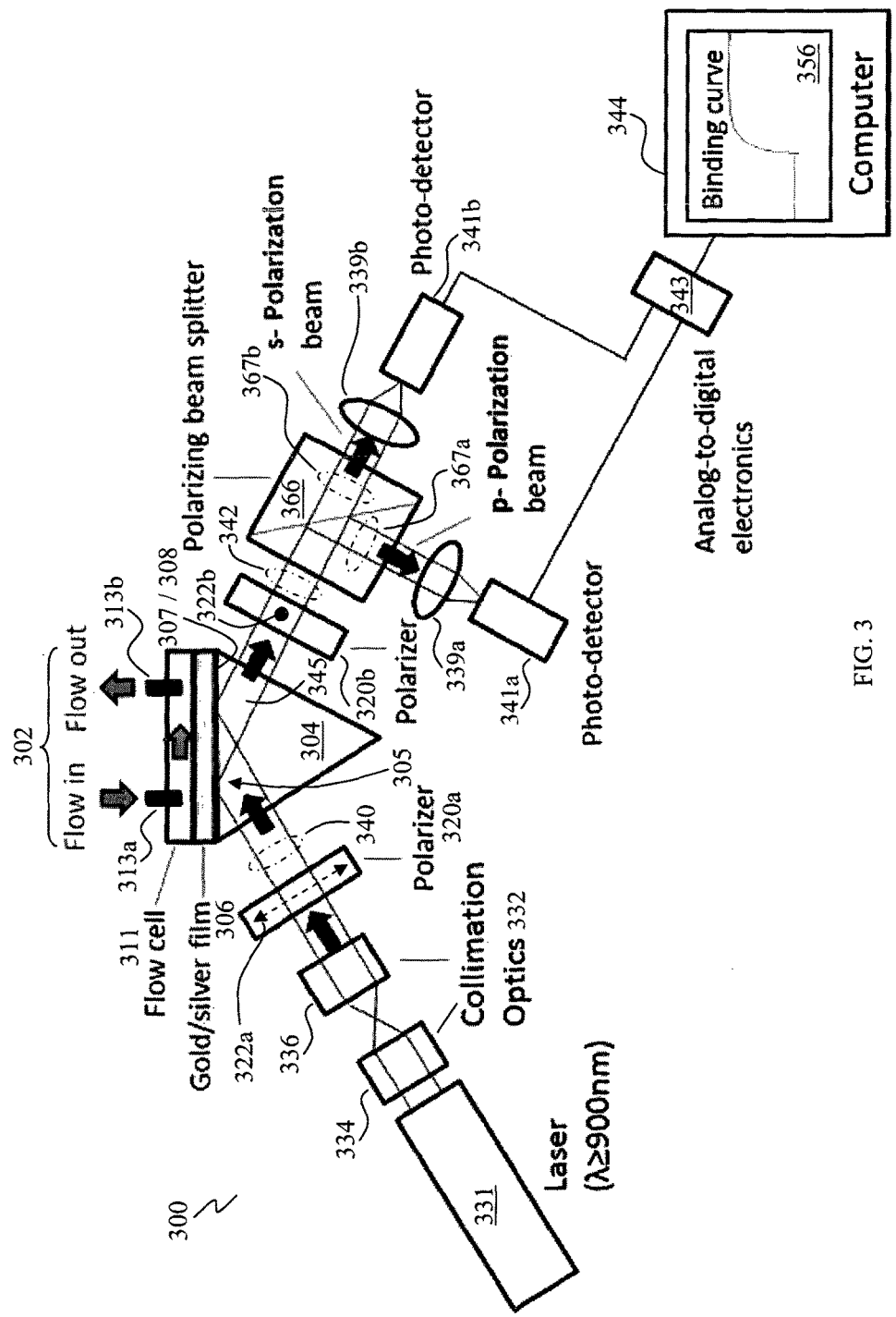
FIG. 3 shows a schematic view of an optical sensing device, according to various embodiments.

FIG. 3 shows a schematic view of an optical sensing device or system 300, according to various embodiments. The sensing device 300 may be a surface plasmon resonance (SPR) imaging sensor, for example, a spectral SPR imaging sensor. The sensing device 300 may employ a method of differential intensity response between the p-polarisation beam (or wave) and the s-polarisation beam (or wave) for SPR detection. Like features or components of the sensing device 300 that are similarly present in the sensing device 200 are denoted by like reference numerals increased by 100, and which may be as correspondingly described in the context of the sensing device 200 and therefore are omitted here.

The sensing device 300 may include a light source 331, for example in the form of a laser, such as a near infrared (IR) laser. The laser may provide a beam having a wavelength, λ, equal to or more than about 850 nm (≥850 nm), e.g., equal to or more than about 900 nm (≥900 nm). The beam emitted by the laser 331 may be collimated and expanded by lenses 334, 336. The collimated beam or incident beam 340, after transmitting through the first polariser 322a, may be incident on the total internal reflection surface 307 of a prism (e.g., a glass prism) 304 provided with an SPR-active element 306 (e.g., a gold or silver/gold sensing layer) having an SPR sensing surface 308.

The SPR sensor arrangement 302 of the sensing device 300 may further include a sampling substrate, for example, in the form of a flow cell 311. The flow cell 311 may be provided or attached to or on the sensor surface 308 for feeding in samples with different refractive index values. The flow cell 311 may include an inlet 313a to allow a sample to flow into the flow cell 311, and an outlet 313b to allow the sample to flow out of the flow cell 311.

The sensing device 300 may further include a polarising beam splitter 366 arranged in the optical path of transmitted light bream 342. This may mean that the polarising beam splitter cube 366 may receive the transmitted light beam 342. The polarising beam splitter 366 may separate or divide the transmitted light beam 342 into a p-polarisation beam (or a p-optical path) 367a and an s-polarisation beam (or an s-optical path) 367b. The polarising beam splitter 366 may be arranged in front of a detector arrangement, for example having a first detector (e.g., a photodetector or a photodiode) 341a and a second detector (e.g., a photodetector or a photodiode) 341b. The p-polarisation beam 367a may be focused by a first focusing lens (e.g., an objective lens) 339a towards the first detector 341a to be detected or captured by the first detector 341a. The s-polarisation beam 367b may be focused by a second focusing lens (e.g., an objective lens) 339b towards the second detector 341b to be detected or captured by the second detector 341b. The first detector 341a and the second detector 341b may be electrically coupled to analog-to-digital electronics or circuit 343 and to a processor (e.g., a computer, or notebook computer) 344. In this way, the respective signals produced by the first detector 341a and the second detector 341b may be converted into respective digital signals by the analog-to-digital electronics 343 and received by the processor 344, for example, to be stored, displayed on a display 356, processed, manipulated, or analysed. In various embodiments, the processor 344 may be employed to perform subtraction of the signal (e.g., p-signal) associated with the p-polarisation beam 367a and the signal (e.g., s-signal) associated with the s-polarisation beam 367b.

The subtraction between the p-signal and the s-signal may cancel the common path noise so that the sensor detection limit may be enhanced, where the detection limit of an SPR device or system may be determined by equation 10.

As described above, the differential measurement scheme employed in the sensing device 300 may involve separating the p- and s-polarisation beams by optics, and the subtraction signal, obtained between the p-signal and the s-signal, may cancel the measurement uncertainty.

While not shown in FIG. 3, it should be appreciated that a quarter-wave (λ/4) plate may be arranged between the prism 304 and the second polariser 320b, for example similar to the arrangement of the quarter-wave (λ/4) plate 251 in the sensing device 250 (FIG. 2B).

The sensing device 300 may provide infrared (IR) detection. As described above, the light source 331 may be a laser operating at near infrared wavelength range beyond 850 nm, which may extend the propagation length of a surface plasmon wave on the SPR sensing surface 308, e.g., a gold sensing surface. This may enhance the response at the resonance condition. According to equation 10, enhancement in the SPR sensor response leads to a lower sensor detection limit.

As also described above, the sensing device 300 may provide a differential response between p- and s-polarisation beams in a polarisation orientation based SPR sensor. The polarising beam splitter cube 366 separates the p-polarisation beam 367a and the s-polarisation beam 367b and both optical signals may be detected in parallel with photodetectors 341a, 341b. At surface plasmon resonance, only a p-polarisation light (e.g., p-polarisation beam 367a) is altered, while an s-polarisation light (e.g., s-polarisation beam 367b) remains unchanged, which therefore may serve as a reference signal in the measurement. The differential signal (subtraction between p- and s-polarisation) may cancel the common path noise. According to equation 10, the suppression in system noise may enhance the sensor stability, which in turn may lead to a lower sensor detection limit.

Results obtained using the sensing devices of various embodiments will now be described by way of the following non-limiting examples.

Figure 4A:
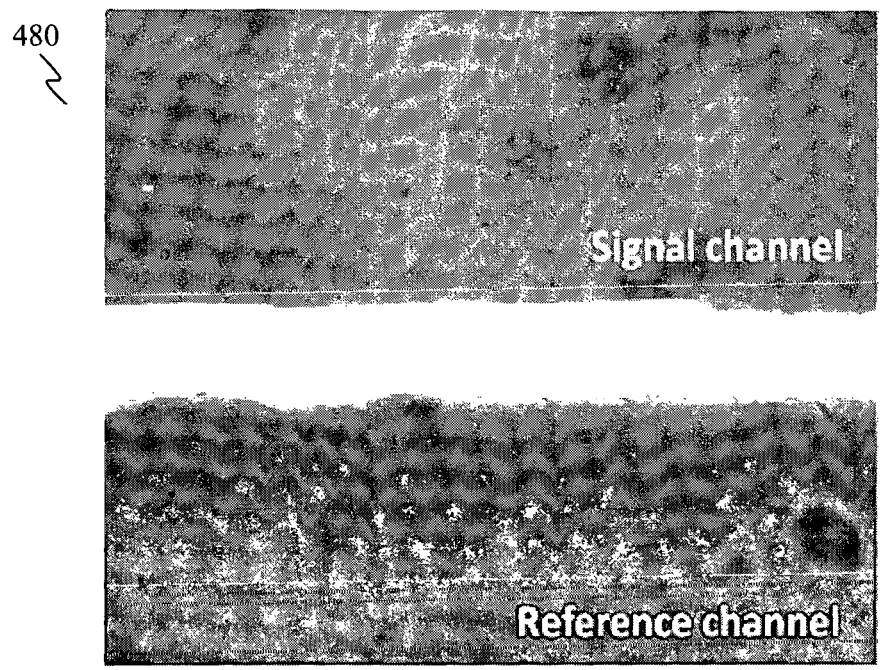
Figure 4B:
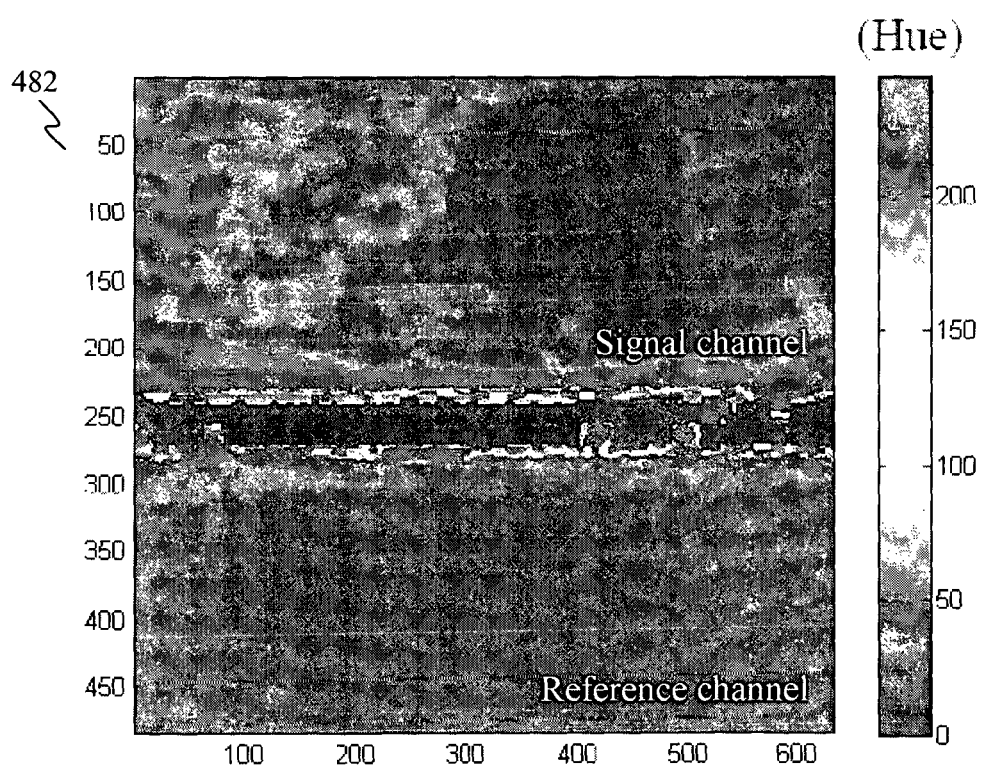
FIG. 4B shows a corresponding image obtained using a HSV (Hue-Saturation-Value) colour space for the SPR image of FIG. 4A.

FIG. 4A shows an example of a colorimetric SPR image 480 that may be obtained when the sensing channel (or signal channel) (e.g., 212a) and the reference channel (e.g., 212b) are filled with a water sample, while FIG. 4B shows a corresponding image 482 obtained using a HSV (Hue-Saturation-Value) colour space for the SPR image 480. The y-axis and the x-axis of FIG. 4B show the respective image pixels in the y-direction and the x-direction.

Figure 5A:
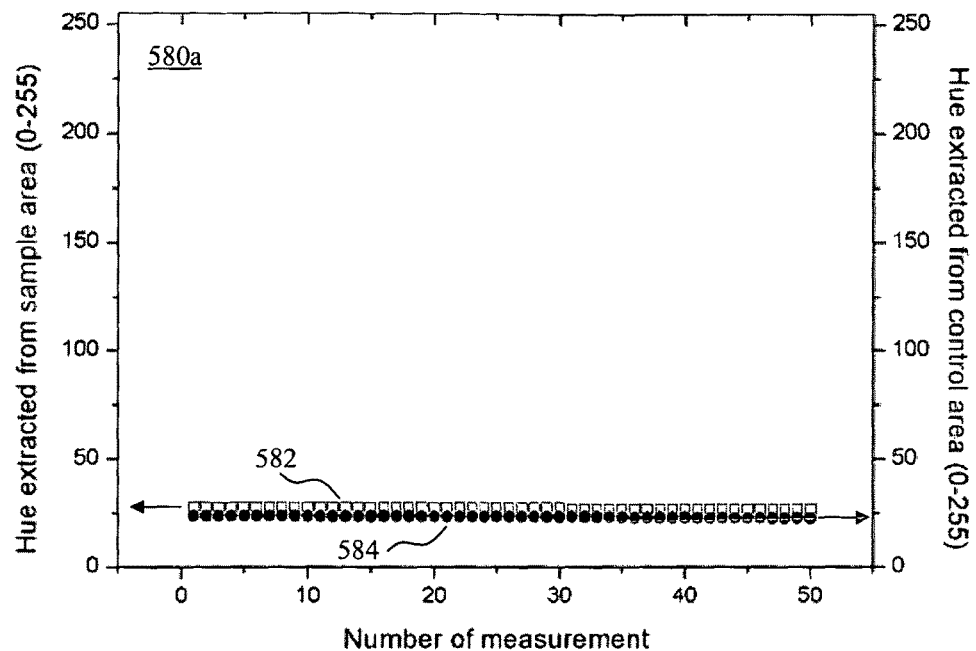
FIG. 5A shows a plot of the extracted Hue values for 50 data points from a sensing channel and a reference channel, both filled with a water sample.
Figure 5B:
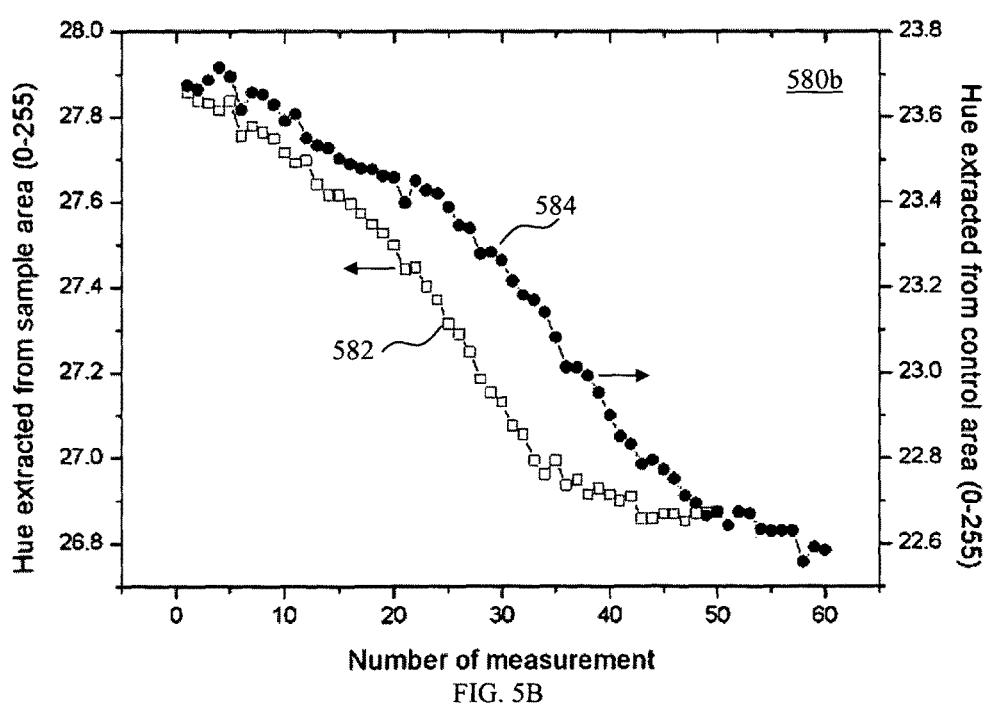
FIG. 5B shows a zoomed-in version of the extracted Hue values of the plot of FIG. 5A.

In various embodiments, the HSV colour space may be applied to extract and quantify the colour variation against time. FIG. 5A shows a plot 580a of the extracted Hue values for 50 data points from a sensing channel (e.g., 212a) and a reference channel (e.g., 212b), both filled with a water sample, where the responses are at least substantially stable. Plots 580a shows the extracted Hue values 582 (representing the sensing signal) corresponding to the sensing channel and the extracted Hue values 584 (representing the reference signal) corresponding to the reference channel. In order to show the small variations within these data, the scale of the y-axis may be reduced to a range of 1.3 Hue values and the results are shown in plot 580b of FIG. 5B. It may be observed that there is a clear response variation against time within the 1.3 Hue range and the trend of the fluctuations are at least substantially similar for the signal and reference channels.

Figure 5C:
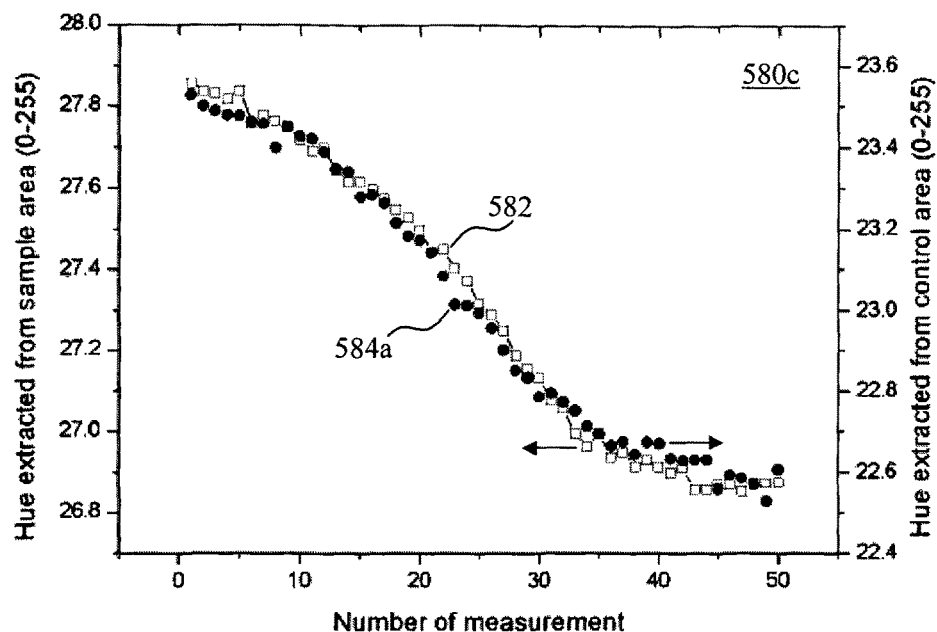

Before the subtraction between the sensing signal 582 and the reference signal 584, the trend of the reference signal 584 may be correlated with that of the signal channel and the resultant curve may be plotted together with the signal 582 from the signal channel, as shown in FIG. 5C illustrating a plot 580c of a sensing signal 582 and a correlated reference signal 584a.

Figure 5D:
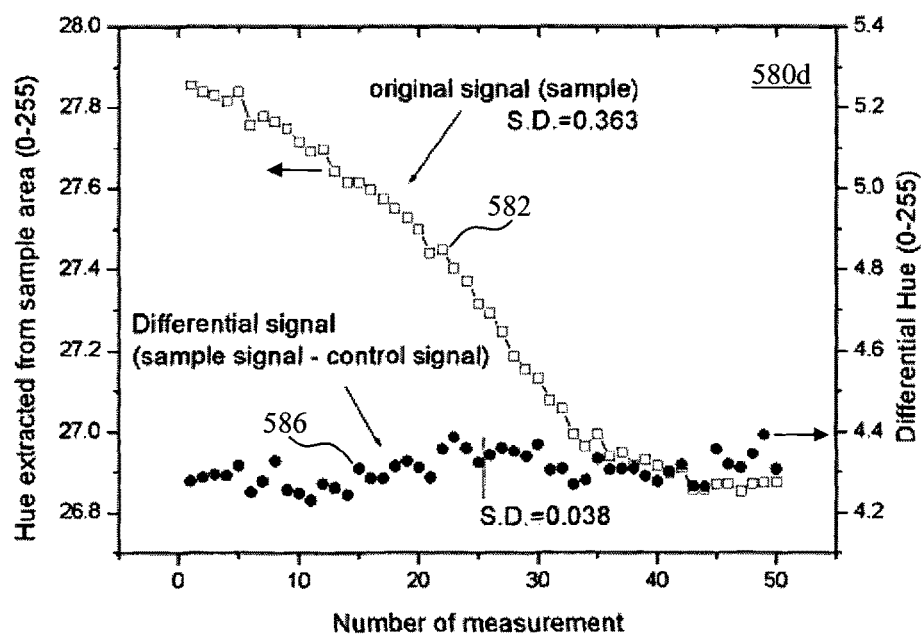
FIG. 5D shows a plot of the sensing signal and a differential signal.

In order to eliminate the common noise, subtraction between the sensing signal (or sample signal) and the reference signal (or control signal) may be performed and the differential signal is as shown in FIG. 5D illustrating a plot 580d of the sensing signal 582 and the differential signal 586. As shown in the plot 580d, the measurement fluctuation has been greatly suppressed by the signal subtraction. The measurement standard deviation (S.D.) of the differential signal 586 is about 0.038 Hue value, which is about 1 order of magnitude lower than that of the original sensing signal 582, where the standard deviation (S.D.) is about 0.363 Hue value.

As would be appreciated, the differential measurement scheme is in the time domain instant, where the measurement uncertainty against time (measurement S.D.) may be reduced by 1 order of magnitude by the application of the differential scheme. The sensor resolution may be dependent on the measurement standard deviation (S.D.), based on Equations 10 and 11. Therefore, a reduced S.D. produces or results in a corresponding sensor resolution improvement.

In order to demonstrate the sensor resolution improvement of the colorimetric SPR imaging sensor of various embodiments employing a differential response, further measurements have been performed using salt solution samples with different refractive index values. The salt solution samples may range from 0% (water), 1%, 2%, 3%, 4% to 5% salt solutions, having the corresponding refractive index values of about 1.3330 RIU, about 1.3347 RIU, about 1.3365 RIU, about 1.3383 RIU, about 1.3400 RIU and about 1.3418 RIU respectively.

FIGS. 6A to 6F show colorimetric SPR images for different salt solution samples. The SPR images show that the colour observed from the signal channel changes from a red colour to a bright green colour when the concentration of the salt solution (or refractive index) increases from 0% (~1.3330 RIU) to about 5% (1.3418 RIU).

Figure 7:
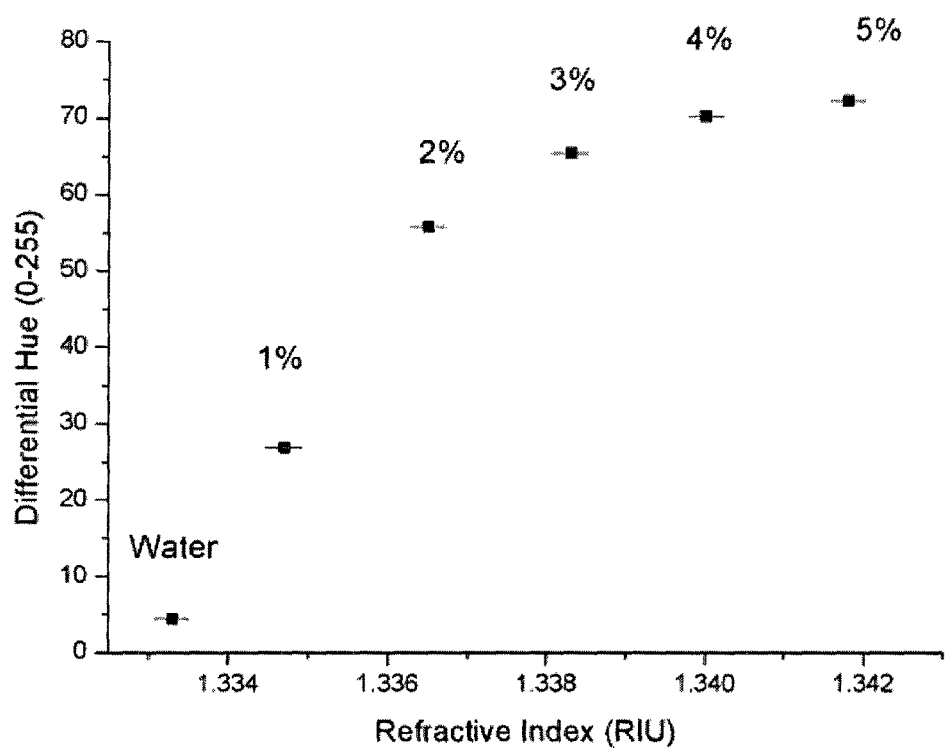
FIG. 7 shows a plot of the sensor response curve obtained based on the SPR images and results for different salt solution samples.

The SPR imaging responses may be further quantified (for example following the processing procedure similar to that described for obtaining the results shown in FIGS. 5A to 5D) and the sensor response curve may be as shown in FIG. 7. From the response curve, the sensitivity (being ΔRIU/response) of the sensor at the refractive index range (1.3330-1.3365 RIU) is about $6.2 \times 10^{-5}$ RIU/Hue.

As shown in FIG. 5D, the measurement standard deviation (S.D.) of a water sample before subtraction is about 0.363 (Hue value) and the sensor resolution, determined using equation 11, is about $2.3 \times 10^{-5}$ RIU (before subtraction). As shown in the same plot 580d of FIG. 5D, the value of S.D. may be reduced to about 0.038 (Hue value) with the application of the differential measurement scheme and the final sensor resolution may be determined, using equation 11, to be about $2.3 \times 10^{-6}$ RIU (differential measurement). Comparing these two values, the differential measurement scheme has demonstrated 1 order of magnitude improvement in the sensor resolution. Further, the sensor resolution ($2.3 \times 10^{-6}$ RIU) of the colorimetric SPR imaging sensor of various embodiments is about 1 order of magnitude better than the resolution of conventional scanning based spectral imaging sensors ($10^{-5}$ RIU) and conventional intensity modulation based imaging sensors ($10^{-5}$ RIU).

As described above for the various embodiments of the sensing device, the prism sensor head (e.g., corresponding to the SPR sensor arrangement) may be placed between two polarisers with perpendicular orientation angles. For the wavelength of the incident beam longer or shorter than the excitation wavelength of the surface plasmon, the light reflected from the SPR sensing surface is blocked by the perpendicular polariser pair. At the resonance wavelength, the excitation of a surface plasmon wave may induce a phase shift between the p-polarisation light and the s-polarisation light. The phase shift may rotate the polarisation ellipse of the beam reflected from the SPR sensing surface and the light in the resonance wavelength range may be partly transmitted. A spectral profile (colour map) may therefore be produced in the SPR image and the colour may be changed with respect to the phase shift induced at surface plasmon resonance.

One or more embodiments may employ a differential response between signal and reference sensing areas in SPR detection. For example, as shown in FIG. 2A, both the signal channel 212a and the reference channel 212b may be arranged on the sensing surface 208. Images from both channels 212a, 212b may be focused on the same CCD chip and captured simultaneously. Signals from both channels 212a, 212b may experience close instrumentation and environmental noise, and therefore the subtraction between them eliminates the common path noise. According to equation 10, the sensor resolution is equal to the sensor sensitivity times the sensor stability, and therefore noise elimination may produce a corresponding enhancement in sensor resolution. The result as described above shows that the measurement standard deviation (S.D.) of a water sample before subtraction is about 0.363 (Hue value) (see plot 580d, FIG. 5D) and the sensor resolution is about $2.3 \times 10^{-5}$ RIU (before subtraction). As shown in the same plot 580d, the value of S.D. is reduced to about 0.038 (Hue value) with the application of a differential measurement scheme between the sensing signal and the reference signal and the final sensor resolution is found to be about $2.3 \times 10^{-6}$ RIU (differential measurement). Comparing these two values, the differential measurement scheme has demonstrated 1 order of magnitude improvement in the sensor resolution. This value is 1 order of magnitude better than the resolution of the conventional scanning based spectral imaging sensor ($10^{-5}$ RIU) and intensity based imaging sensor ($10^{-5}$ RIU) reported.

One or more embodiments may employ a differential intensity response between p- and s-polarisations in SPR detection. For example, as shown in FIG. 3, the polarising beam splitter cube 366 separates the p-polarisation beam 367a and the s-polarisation beam 367b and both optical signals (or lights) are detected in parallel with photodetectors 341a, 341b. At surface plasmon resonance, only the p-polarisation light 367a is altered, while the s-polarisation light 367b remains unchanged, which may therefore serve as the reference signal. The differential signal between these two polarisation lights may therefore cancel the common path noise. According to equation 10, the suppression in system noise may enhance the sensor stability, which leads to a lower sensor detection limit.

One or more embodiments may incorporate the application of a near infrared laser at wavelengths beyond about 850 nm for SPR detection. An infrared laser may operate at a near infrared wavelength range beyond 850 nm, which may extend the propagation length of surface plasmon wave at resonance on an SPR sensing surface (e.g., a gold sensing surface). This may provide an enhanced SPR response. According to equation 10, the enhancement in the SPR sensor response leads to a lower sensor detection limit. The near infrared wavelength range between about 850 nm and about 1000 nm at least substantially matches the response peak of silicon based photo-detectors, which are the most widely used and low-cost photo-detectors.

It should be appreciated that the SPR sensor design of various embodiments, with enhanced detection limit (e.g., sensing device 300, FIG. 3), may find potential applications, for example, in drug discovery and biomarker detection, which are areas that require sensitive analytical measurements.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An optical sensing device for surface plasmon resonance (SPR), the optical sensing device comprising:
   a first polariser;
   a second polariser, wherein the first polariser and the second polariser have respective transmission axes aligned in orthogonal directions;
   an SPR sensor arrangement comprising an SPR sensing surface, the SPR sensor arrangement arranged to receive an incident light beam passed through the first polariser to be reflected at the SPR sensing surface and transmitted through the second polariser to provide a transmitted light beam;
   wherein a sensing area and a reference area are defined on the SPR sensing surface, and wherein the sensing signal originates from the sensing area and the reference signal originates from the reference area;
   a detector arrangement configured to detect the transmitted light beam, the transmitted light beam comprising a sensing signal and a reference signal; and
   a processor electrically coupled to the detector arrangement, the processor configured to perform a subtraction operation between the sensing signal and the reference signal.

2. The optical sensing device as claimed in claim 1, wherein the SPR sensor arrangement comprises a prism, and wherein the SPR sensing surface is provided on a base of the prism.

3. The optical sensing device as claimed in claim 1, further comprising a polarising beam splitter configured to split the transmitted light beam into a p-polarisation beam to define the sensing signal, and a s-polarisation beam to define the reference signal.

4. The optical sensing device as claimed in claim 3, wherein the detector arrangement comprises a first detector configured to detect the p-polarisation beam, and a second detector configured to detect the s-polarisation beam.

5. The optical sensing device as claimed in claim 1, wherein the detector arrangement comprises a colour CCD detector.

6. The optical sensing device as claimed in claim 1, further comprising a quarter-wave plate arranged in an optical path between the SPR sensor arrangement and the second polariser.

7. The optical sensing device as claimed in claim 1, further comprising a light source configured to provide a light for generating the incident light beam.

8. The optical sensing device as claimed in claim 1, wherein the processor is further configured to extract respective Hue component values from the sensing signal and the reference signal based on a Hue-Saturation-Value colour space model prior to performing the subtraction operation.

9. An optical sensing method using surface plasmon resonance (SPR), the method comprising:
   providing a sample to an SPR sensing surface of an SPR sensor arrangement; passing a light through a first polariser to provide an incident light beam to be received by the SPR sensor arrangement;
   reflecting the incident light beam at the SPR sensing surface to provide a reflected light beam;
   transmitting the reflected light beam through a second polariser to provide a transmitted light beam, wherein the first polariser and the second polariser have respective transmission axes aligned in orthogonal directions;
   wherein a sensing area and a reference area are defined on the SPR sensing surface, and wherein the sensing signal originates from the sensing area and the reference signal originates from the reference area;
   detecting the transmitted light beam, the transmitted light beam comprising a sensing signal and a reference signal; and
   performing a subtraction operation between the sensing signal and the reference signal.

10. The optical sensing method as claimed in claim 9, wherein the SPR sensor arrangement comprises a prism, and wherein the SPR sensing surface is provided on a base of the prism.

11. The optical sensing method as claimed in claim 9, further comprising splitting the transmitted light beam into a p-polarisation beam to define the sensing signal, and a s-polarisation beam to define the reference signal.

12. The optical sensing method as claimed in claim 11, wherein detecting the transmitted light beam comprises detecting the p-polarisation beam and the s-polarisation beam.

13. The optical sensing method as claimed in claim 9, further comprising extracting respective Hue component values from the sensing signal and the reference signal based on a Hue-Saturation-Value colour space model prior to performing the subtraction operation.

14. An optical sensing device for surface plasmon resonance (SPR), the optical sensing device comprising:
   a first polariser;
   a second polariser, wherein the first polariser and the second polariser have respective transmission axes aligned in orthogonal directions;
   an SPR sensor arrangement comprising an SPR sensing surface, the SPR sensor arrangement arranged to receive an incident light beam passed through the first polariser to be reflected at the SPR sensing surface and transmitted through the second polariser to provide a transmitted light beam;
   wherein a sensing area and a reference area are defined on the SPR sensing surface, and wherein the sensing signal originates from the sensing area and the reference signal originates from the reference area;

an optics arrangement configured to split the transmitted light beam into a p-polarisation beam and a s-polarisation beam; and a detector arrangement configured to detect the p-polarisation beam and the s-polarisation beam;

a processor electrically coupled to the detector arrangement, wherein the p-polarisation beam defines a sensing signal, and the s-polarisation beam defines a reference signal, and wherein the processor is configured to perform a subtraction operation between the sensing signal and the reference signal.

15. The optical sensing device as claimed in claim 14, wherein the optics arrangement comprises a polarising beam splitter.

16. The optical sensing device as claimed in claim 14, wherein the detector arrangement comprises a first detector configured to detect the p-polarisation beam, and a second detector configured to detect the s-polarisation beam.

17. The optical sensing device as claimed in claim 14, wherein the SPR sensor arrangement comprises a prism, and wherein the SPR sensing surface is provided on a base of the prism.

18. The optical sensing device as claimed in claim 7, wherein the light source comprises a broad band light source.

* * * * *